United States Patent
Achkar

(12)
(10) Patent No.: US 6,552,009 B2
(45) Date of Patent: *Apr. 22, 2003

(54) COMPOSITIONS AND METHODS OF TREATING ABNORMAL CELL PROLIFERATION

(75) Inventor: Charles C. Achkar, North Bergen, NJ (US)

(73) Assignee: Gentrix LLC, North Bergen, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/872,662

(22) Filed: Jun. 1, 2001

(65) Prior Publication Data

US 2001/0049365 A1 Dec. 6, 2001

Related U.S. Application Data

(63) Continuation-in-part of application No. 09/351,020, filed on Jul. 12, 1999, now Pat. No. 6,242,435, which is a continuation-in-part of application No. 09/116,632, filed on Jul. 16, 1998, now abandoned.

(51) Int. Cl.[7] ............... A61K 31/07; A61K 31/592; A61K 31/593
(52) U.S. Cl. ........................... 514/168; 514/725
(58) Field of Search ................. 514/168, 725

(56) References Cited

U.S. PATENT DOCUMENTS

| 4,866,048 A | 9/1989 | Calverly et al. ............. 514/167 |
| 5,514,672 A | 5/1996 | Bazzano .................... 514/168 |
| 5,547,947 A | 8/1996 | Dore et al. ................. 514/167 |
| 5,786,391 A | 7/1998 | Gudas et al. ............... 514/690 |

FOREIGN PATENT DOCUMENTS

| CA | 2096196 | 5/1993 |
| CA | 2096196 | 11/1993 |
| EP | 0579915 | 1/1994 |
| EP | 704210 | 4/1996 |
| FR | 2714595 | 7/1995 |
| JP | 63060910 | 3/1988 |
| WO | WO8402845 | 8/1984 |
| WO | 0512814 | 11/1992 |
| WO | WO9640154 | 12/1996 |
| WO | 9709987 | 2/1997 |

OTHER PUBLICATIONS

Carlberg et al., "Vitamin D–Retinoid Association: Molecular Basis and Clinical Applications", J. Invest. Dermatol. Symp. Proc., 1(1), 82–86, 1996.

R. Ceovic et al., "Calciprotiol—A Vitamin D3 Analogue (MC 903) in the Treatment of Psoriasis Vulgaris: A Review", Acta Dermatovenerologica Alpina, Panonica et Adriatica, 7/2, 67–77, 1998 (abstract).

S. Segaert et al., "Retinoic Acid Modulates the Anti-Proliferation Effect of 1,25–dihydroxyvitamain D3 in Cultured Human Epidermal keratinocytes," J. Invest. Dermatol., 109/1, 46–54, 1997.

M. Skopinska et al., "Calcitriol and Isotretinoin Combined Therapy for Precancerous and Cancerous Skin Lesions," J. Dermatol. Treatment, 8/1, 5–10, 1997.

A. Bargagna et al., "TLC, HPTLC and HPLC Determination of Cis– and Trans–retinoic Acids, Retiniol and Retinyl Acetate in Topically Applied Products," Acta. Tachnol. Legis Med., 2(2), 75–86, 1991.

Van Der Vleuten et al., "In–Patient Treatment with Calcipotriol Versus Dithranol in Refractory Psoriasis", Eur. J. Dermatol., 5(8), 676–679, 1995 (abstract).

Primary Examiner—Phyllis G. Spivack

(57) ABSTRACT

A composition is described comprising a vitamin D analog and a retinoid wherein: (a) the vitamin D analog is capable of binding a vitamin D receptor or being converted in vivo into a compound capable of binding a vitamin D receptor; and (b) the retinoid is selected from the group consisting of retinol in a concentration of at least about 1.0% and a retinoid characterized by having a substitution at the 4-position. Further, methods of treating disorders characterized by abnormal cell-proliferation and/or cell-differentiation are also described.

53 Claims, No Drawings

COMPOSITIONS AND METHODS OF TREATING ABNORMAL CELL PROLIFERATION

RELATED APPLICATIONS

This application is a continuation-in-part of U.S. Ser. No. 09/351,020, filed Jul. 12, 1999 now U.S. Pat. No. 6,242,435, which is a continuation-in-part of U.S. Ser. No. 09/116,632, filed Jul. 16, 1998 abandoned.

Throughout this application, various references are referred to within parentheses. Disclosures of these publications in their entireties are hereby incorporated by reference into this application to more fully describe the state of the art to which this invention pertains.

FIELD OF THE INVENTION

The present invention relates to compositions comprising certain retinoids and vitamin D analogs useful in inducing differentiation and inhibiting undesirable proliferation of cells, such as cancer cells and skin cells. The present invention also relates to methods of using the above compositions in the treatment of diseases and conditions characterized by abnormal cell differentiation and/or cell proliferation.

DESCRIPTION OF THE RELATED ART

Abnormal cell differentiation and/or cell differentiation is associated with many conditions and diseases. For instance, hyperproliferation of epithelial cells is associated with psoriasis which causes the skin to shed itself too rapidly, every three to four days. The goal in treating psoriasis is to reduce inflammation and to slow down rapid skin cell division.

U.S. Pat. No. 4,866,048 discloses that certain vitamin D derivatives, in particular calcitriol (1 alpha,25-dihydroxy-vitamin $D_3$ or) and calcipotriol are able to stimulate the differentiation of cells and inhibit excessive cell proliferation, and it has been suggested that these compounds are useful in the treatment of diseases characterized by abnormal cell differentiation and/or cell differentiation such as leukemia, myelofibrosis, psoriasis and acne.

Certain retinoids are also known for their antiproliferative and differentiation activity. For instance, retinol (vitamin A) is an endogenous compound which occurs naturally in the human body and is essential for normal cell differentiation of certain cell types such as epithelial cells. Retinoic acid is believed to be an active derivative of retinol. Thus, retinoic acid is believed to be more effective than retinol and retinyl esters at providing skin benefits.

Natural and synthetic vitamin A derivatives (including retinoic acid) have been used extensively in the treatment of a variety of skin and hyperproliferation disorders. For example, retinoic acid has been employed to treat certain types of leukemia like acute apromyelocytic leukemia as well as a variety of skin conditions such as acne, wrinkles, psoriasis, age spots and discoloration (Vahlquist, A. et al., *J. Invest. Dermatol.*, Vol. 94, Holland D. B. and Cunliffe, W. J. (1990), pp. 496–498; Ellis C. N. et al., "Pharmacology of Retinols in Skin", Vasel, Karger, Vol. 3, (1989), pp.249–252; Lowe, N. J. et al., Vol. 3, (1989), pp. 240–248; PCT Patent Application No. WO 93/19743). Although retinoids have been viewed classically as cancer prevention agents, considerable laboratory evidence supports their testing as anti-tumor drugs as well (Cancer Treat Rep 1987; 71: 493–515 May, 1987).

It is important to note that while clinical experience with either retinoids or vitamin D derivatives against conditions associated with abnormal cell differentiation and/or cell differentiation has met with certain amount of success in some instances, these compounds have frequently been unable to provide the desired clinical results.

For instance, the synthetic Vitamin D, calcipotriol, or retinoic acid which are available in prescription form are somewhat useful for individuals with localized psoriasis. However, these compound are not very effective on most patients.

Therapeutic regimens for acne involve local and systemic therapies, although the former is indicated in the vast majority of cases. Topical application of a variety of chemical application which include mainly sulfur, resorcinol, salicylic acid, benzoyl peroxide, and retinoic acid are frequently used to treat acne. All the foregoing agents are known as "peeling" or "drying" agents which are believed to exert their therapeutical effect by causing erythema, irritation, and desquamation of the skin to expel comedones. The therapeutic efficacy of these agents, however, is rather variable, and their utility is limited partially because of the irritation caused by their application (see U.S. Pat. No. 3,932,665). Oral formulations of retinoic acid are also used but serious side effects are associated with the oral use of this compound including severe fetal malformation in pregnant women.

SUMMARY OF THE INVENTION

The present invention provides compositions comprising certain vitamin D and retinoid compounds which are useful for the treatment of disorders characterized by abnormal cell-proliferation and/or cell-differentiation.

Specifically, the present invention provides a composition comprising a vitamin D analog and a retinoid, wherein:

(a) the vitamin D analog is capable of binding a vitamin D receptor or being converted in vivo into a compound capable of binding a vitamin D receptor; and (b) the retinoid is selected from the group consisting of retinol in a concentration of at least about 1.0% by weight, a compound in a concentration of at least about 1.0% by weight capable of being converted in vivo into retinol, retinoid D with an alcohol $CH_2OH$ terminal side chain, retinoid D with an ester at the terminal side chain, retinoid D with an ether at the terminal side chain, retinoid D with an aldehyde at the terminal side chain, and retinoid D with a carboxylic acid at the terminal side chain, wherein retinoid D with the alcohol $CH_2OH$ terminal side chain has the structure:

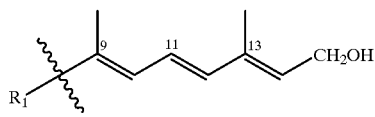

wherein the configuration at the 7-, 9-, 11- and 13-position double bonds is independently Z or E and wherein $R_1$ is selected from the group consisting of

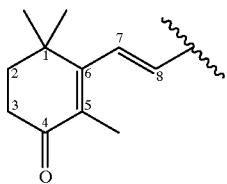

wherein the keto group at the 4-position is free or protected, or is replaced by a thioketone group which is free or protected or is replaced by $C_{1-6}$-alkylidene group;

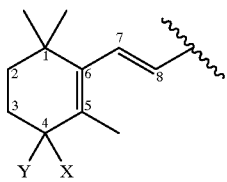

wherein X is selected from the group consisting of hydrogen and $C_{1-6}$-alkyl and Y is selected from the group consisting of $C_{1-6}$-alkyl, hydroxyl, alkoxyl, acyloxyl, halide, azide, sulfhydryl, amine and $C_{1-6}$-alkyl substituted amino and wherein the absolute configuration at the 4-position is independently R or S;

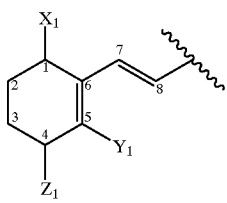

wherein $X_1$, $Y_1$ are independently selected from the group consisting of hydrogen, $C_{1-6}$-alkyl, hydroxyl, alkoxyl, acyloxyl, halide, azide, sulfhydryl, amine and $C_{1-6}$-alkyl substituted amino and $Z_1$ is selected from the group consisting of $C_{1-6}$-alkyl, hydroxyl, alkoxyl, acyloxyl, halide, azide, sulfhydryl, amine and $C_{1-6}$-alkyl substituted amino;

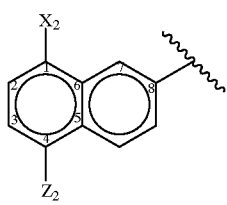

wherein $X_2$ is selected from the group consisting of hydrogen, $C_{1-6}$-alkyl, hydroxyl, alkoxyl, acyloxyl, halide, azide, sulfhydryl, amine and $C_{1-6}$-alkyl substituted amino and $Z_2$ is selected from the group consisting of $C_{1-6}$-alkyl, hydroxyl, alkoxyl, acyloxyl, halide, azide, sulfhydryl, amine and $C_{1-6}$-alkyl substituted amino;

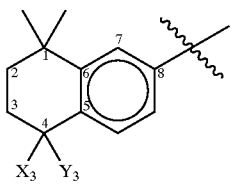

wherein $X_3$ and $Y_3$ are independently selected from the group consisting of hydrogens, $C_{1-6}$-alkyl, hydroxyl, alkoxyl, acyloxyl, halide, azide, sulfhydryl, amine and $C_{1-6}$-alkyl substituted amino so long as $X_3$ and $Y_3$ are not both hydrogens.

The present inventions also provides methods for treating various conditions associated with abnormal cell proliferation and/or abnormal cell differentiation.

DETAILED DESCRIPTION OF THE INVENTION

In accordance with the invention, It has been surprisingly discovered that a composition comprising a vitamin D analog and a certain retinoid is useful in treating a subject suffering from a disorder characterized by abnormal cell-proliferation and/or cell-differentiation more effectively than either a composition comprising a vitamin D or the above retinoid or a composition comprising a vitamin D analog with other types of retinoids.

The retinoid used in the composition of the present invention is selected from the group consisting of retinol in a concentration of at least about 1.0% by weight, a compound in a concentration of at least about 1.0% by weight capable of being converted in vivo into retinol, retinoid D with an alcohol $CH_2OH$ terminal side chain, retinoid D with an ester at the terminal side chain, retinoid D with an ether at the terminal side chain, retinoid D with an aldehyde at the terminal side chain, and retinoid D with a carboxylic acid at the terminal side chain, wherein retinoid D with the alcohol $CH_2OH$ terminal side chain has the structure:

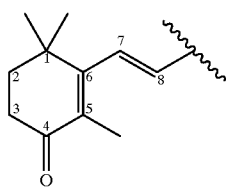

wherein the configuration at the 7-, 9-, 11- and 13-position double bonds is independently Z or E and wherein $R_1$ is selected from the group consisting of

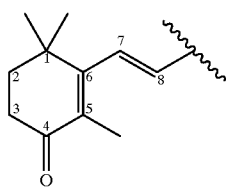

wherein the keto group at the 4-position is free or protected, or is replaced by a thioketone group which is free or protected or is replaced by $C_{1-6}$-alkylidene group;

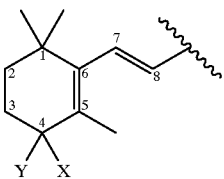

wherein X is selected from the group consisting of hydrogen and $C_{1-6}$-alkyl and Y is selected from the group consisting of $C_{1-6}$-alkyl, hydroxyl, alkoxyl, acyloxyl, halide, azide, sulfhydryl, amine and $C_{1-6}$-alkyl substituted amino and wherein the absolute configuration at the 4-position is independently R or S;

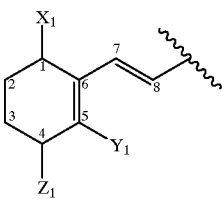

wherein $X_1$, $Y_1$ are independently selected from the group consisting of hydrogen, $C_{1-6}$-alkyl, hydroxyl, alkoxyl, acyloxyl, halide, azide, sulfhydryl, amine and $C_{1-6}$-alkyl substituted amino and $Z_1$ is selected from the group consisting of $C_{1-6}$-alkyl, hydroxyl, alkoxyl, acyloxyl, halide, azide, sulfhydryl, amine and $C_{1-6}$-alkyl substituted amino;

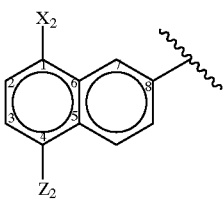

wherein $X_2$ is selected from the group consisting of hydrogen, $C_{1-6}$-alkyl, hydroxyl, alkoxyl, acyloxyl, halide, azide, sulfhydryl, amine and $C_{1-6}$-alkyl substituted amino and $Z_2$ is selected from the group consisting of $C_{1-6}$-alkyl, hydroxyl, alkoxyl, acyloxyl, halide, azide, sulfhydryl, amine and $C_{1-6}$-alkyl substituted amino;

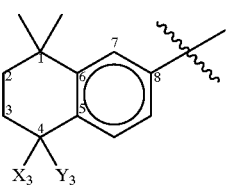

wherein $X_3$ and $Y_3$ are independently selected from the group consisting of hydrogens, $C_{1-6}$-alkyl, hydroxyl, alkoxyl, acyloxyl, halide, azide, sulfhydryl, amine and $C_{1-6}$-alkyl substituted amino so long as $X_3$ and $Y_3$ are not both hydrogens.

Preferably, the abnormal cell proliferation treated with the composition of the present invention is associated with cancer cells and more preferably with skin cancer such as melanoma. Also more preferably, the abnormal cell proliferation is associated with cancer cells that can at least partially respond to hormone or retinoid treatment.

The present invention also provides a method of treating a subject suffering from a disorder selected from the group consisting of psoriasis, acne, atopic dermatitis, eczema, rosacea, actinic keratosis, seborrheic dermatitis, and congenital keratinization disorders, in which any composition of the present invention is administered to the subject in need of such treatment. Preferably, the disorder is psoriasis, eczema, or acne.

The present invention further provides a method of treating one or more conditions of the skin selected from the group consisting of dry skin, photodamaged skin, age spots, aged skin, increasing stratum corneum flexibility, wrinkles, fine lines, actinic blemishes, skin dyschromias, and ichthyosis, comprising applying to the skin having said one or more condition any composition of the present invention. Preferably, the skin condition is actinic blemishes or fine wrinkles.

The present invention also provides methods for preventing or treating individuals suffering hair loss such as male pattern baldness or female pattern baldness comprising applying to the affected areas of the skin any composition of the present invention.

The present invention further provides methods for restoring the natural color of gray hair comprising applying to the affected areas of the skin any composition of the present invention.

For the purpose of this invention, treatment of a subject with the composition of the present invention means administering or applying to said subject either together or separately both the vitamin D analog and the retinoid as defined in the composition of the present invention. Thus, the vitamin D analog and the retinoid may be administered or applied together or separately using either the same or different forms of administration or application.

Also, for the purpose of this invention, the term "vitamin D analog" is defined as a compound capable of binding a vitamin D receptor (not necessarily all) or being converted in vivo into a compound capable of binding a vitamin D receptor (not necessarily all). The term "vitamin D analog" includes but is not limited to vitamin $D_2$ and vitamin $D_3$ derivatives such as cholecalciferol, calcifediol, calcitriol, calcipotriol, ergosterol, ergocalciferol, dihydrotachysterol, 1,25-dihydroxyergocalciferol, 25-hydroxydihydrotachysterol, and the vitamin D analogs disclosed in U.S. Pat. No. 4,866,048. Preferred analogs are cholecalciferol, calcifediol, calcitriol, calcipotriol and the vitamin D analogs disclosed in U.S. Pat. No. 4,866,048. More preferred analogs are cholecalciferol, calcifediol, calcitriol and calcipotriol. Most preferred analogs are calcitriol and calcipotriol.

The concentration of the vitamin D analog may vary from about 0.0001% to about 10% by weight of the total composition of the invention. Preferably, the concentrations employed of vitamin D analogs that can directly bind to the vitamin D receptors, range from about 0.0001% to about 1%, more preferably from about 0.0005% to about 0.05%, still more preferably from about 0.009% to about 0.5%, yet still more preferably from about 0.001 to about 0.008%, and most preferably at about 0.005%.

Preferably, the concentration employed of vitamin D analogs that can be converted in vivo to a compound capable of binding a vitamin D receptor is from about 0.001% to about 10%, more preferably from about 0.01% to about 8%, still more preferably from about 1% to about 6%, and most preferably from about 2% to about 5%.

Retinoid D is preferably 4-oxo-retinoic acid, 4-oxo-retinol, and 4-oxo-retinal, 4-hydroxy-retinol, 4-hydroxyretinal, 4-oxo-retinyl ester, and 4-hydroxyretinyl ester. The most preferred retinoid is 4-oxo-retinol. Preferably, the concentration of retinoid D in the compositions of the invention ranges from about 0.001% to about 1%, more preferably from about 0.025% to about 0.1%, most preferably about 0.05%.

Also, for the purpose of this invention, the term "retinol" includes but is not limited to the following: all-trans-retinol, 13-cis-retinol, 1-cis-retinol, 9-cis-retinol, 3,4-didehydro-retinol. Preferred isomers are all-trans-retinol, 13-cis-retinol, 3,4-didehydro-retinol, and 9-cis-retinol. Most preferred is all-trans-retinol due to its wide commercial availability. The concentration employed of retinol is at least about 0.1%, preferably at least 0.3% by weight of the total weight of the composition. More preferably, the concentration such retinoid is from about at 0.3% to about 20%, more preferably from about 0.5% to about 15%, still more preferably from about 0.5% to about 10%, still more preferably from about 1% to about 10%, still more preferably from about 2% to about 10%, and most preferably about 5%.

The retinoids that can be converted in vivo to retinol include but are not limited to retinyl esters, retinyl-glucoronides, retinal, 3,4-didehydro-retinol. Compounds that are converted spontaneously by isomerization are also included in the compounds of the invention.

Retinyl ester is an ester of retinol and is capable of being converted in vivo into retinol. Retinyl esters suitable for use in the present invention include but are not limited to $C_1$–$C_{30}$ esters of retinol, preferably $C_2$–$C_{20}$ esters, and most preferably $C_2$, $C_3$, and $C_6$ esters because they are commonly available. Examples of retinyl, esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadecanoate, retinyl stearate, retinyl isostearate, retinyl nonadecanoate, retinyl arachidonate, retinyl behenate, retinyl linoleate, and retinyl oleate.

The preferred retinyl esters for use in the present invention are retinyl palmitate, retinyl acetate, retinyl propionate and retinyl linoleate. More preferred retinyl esters are retinyl palmitate and retinyl acetate, the most preferred retinyl ester is retinyl palmitate.

The concentration employed of the retinoid that can be converted in vivo to retinol is at least about 0.1%, preferably at least 0.3% by weight of the total weight of the composition. More preferably, the concentration such retinoid is from about at 0.3% to about 20%, more preferably from about 0.5% to about 15%, still more preferably from about 0.5% to about 10%, still more preferably from about 1% to about 10%, still more preferably from about 2% to about 10%, and most preferably about 5%.

It has also been surprisingly discovered that a composition comprising retinol in a concentration of at least about 1.5% or a compound in a concentration of at least about 1.5% capable of being converted in vivo into retinol is as effective as retinoic acid in treating one or more conditions of the skin selected from the group consisting of dry skin, photodamaged skin, age spots, aged skin, increasing stratum corneum flexibility, wrinkles, fine lines, actinic blemishes, skin dyschromias, ichthyosis and acne. The term "retinol" and the compounds capable of being converted into retinol has been defined above. Preferably, for this composition, the concentration employed of retinol or of the compound capable of being converted in vivo into retinol is at least about 1.8%, more preferably at least about 2% by weight of the total weight of the composition. More preferably, the concentration such retinoid is from about at 2% to about 20%, more preferably from about 2% to about 15%, still more preferably from about 2% to about 10%, and most preferably about 5%.

The compositions of the present invention are preferably topical and/or pharmaceutical. They may be in the form of a cream, ointment, and gel. They may also comprise a cosmetically acceptable vehicle to act as a diluent, dispersant or carrier for the active components in the composition, so as to facilitate their distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the emulsion, and can, in the absence of other cosmetic adjuncts, form the balance of the composition.

An oil or oily material may be present in the claimed compositions, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Various types of active ingredients may be present in cosmetic compositions of the present invention. Actives are defined as skin benefit agents other than emollients and other than ingredients that merely improve the physical characteristics of the composition. Although not limited to this category, general examples include sunscreens and tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells (in keratinocytes, EFA deficiency makes cells hyperproliferative). Supplementation of EFA corrects this. EFAs also enhance lipid biosynthesis of epidermis and provide lipids for the barrier formation of the epidermis. The essential fatty acids are preferably chosen from linoleic acid, gamma-linolenic acid, homo-gamma-linolenic acid, columbinic acid, eicosa-(n-6,9,13)-trienoic acid, arachidonic acid, gamma-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers, perfumes and preservatives (e.g., imidazolidinyl urea, dimethyl imidazolidinone and diazolidinyl urea). Amounts of these materials may range anywhere from 0.001% up to 20% by weight of the composition.

The composition according to the invention is intended primarily but not exclusively as a product for topical application to human skin and as a product to modulate cell differentiation. In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLE 1

This example compares therapeutically applied retinyl palmitate, retinoic acid, calcitriol, and combinations thereof in a cream at different concentrations with the effectiveness of the cream without any of the above compounds present in treating acne. The base cream used to prepare the experimental formulations is the commercially available LUBRIDERM cream. The different compounds at different concentrations were added to the cream and mixed very well. Sixty six volunteers were recruited and were randomly assigned to each of the groups. the subjects were selected on the basis of their having moderate to severe papular-pustular acne. Each group consisted of 3 males and 3 females. No other acne treatment was permitted during the period. Preparations were applied to the face in the morning and evening after washing the face with ordinary soap. Observations were made at time 0, 1, 4, and 8 weeks to assure that treatment was carried out according to direction. Judgments of "worse", "no change", "mild", and "good" were made after 8 weeks of treatment. Table 1 illustrates the results.

TABLE 1

Results of treatment with various compounds on acne

| Treatment | worse | no change | mild | good |
|---|---|---|---|---|
| Control | 2 | 4 | 0 | 0 |
| 0.1% retinoic acid | 0 | 2 | 3 | 1 |
| 0.1% retinyl palmitate | 2 | 3 | 1 | 0 |
| 1% retinyl palmitate | 0 | 4 | 2 | 0 |
| 1.5% retinyl palmitate | 0 | 1 | 3 | 2 |
| 5% retinol | 0 | 1 | 2 | 3 |
| 10% retinol | 0 | 0 | 3 | 3 |
| 0.0025% calcitriol | 2 | 3 | 1 | |
| 0.1% retinoic acid and 0.0025% calcitriol | 0 | 1 | 3 | 2 |
| 0.1% retinyl palmitate and 0.0025% calcitriol | 1 | 2 | 2 | 1 |
| 0.5% retinyl palmitate and 0.0025% calcitriol | 0 | 1 | 3 | 2 |
| 5% retinyl palmitate and 0.0025% calcitriol | 0 | 0 | 1 | 5 |
| 0.1% 4-oxo-retinol | 0 | 1 | 4 | 1 |

TABLE 1-continued

Results of treatment with various compounds on acne

| Treatment | worse | no change | mild | good |
|---|---|---|---|---|
| 0.1% 4-oxo-retinol and 0.0025% calcitriol | 0 | 0 | 3 | 3 |

Table 1 illustrates that retinyl palmitate in concentrations at about 1.5% and more shows a remarkable improvement over lower concentrations in treating acne. In addition, the combination of 4-oxo-retinol and calcitriol shows a synergistic effect when compared with either 4-oxo-retinol and calcitriol alone. A synergistic effect is also seen when calcitriol is combined with retinyl palmitate particularly at concentrations of 0.5% of retinyl palmitate.

The use of each of retinoic acid and calcitriol caused skin irritation while the use of retinyl palmitate or 4-oxo-retinol did not.

EXAMPLE 2

This example compares therapeutically applied retinyl palmitate, retinoic acid, calcitriol, and combinations thereof in a cream at different concentrations with the effectiveness of the cream without any of the above compounds present in treating psoriasis. The base cream used to prepare the experimental formulations is the commercially available LUBRIDERM cream. The different compounds at different concentrations were added to the cream and thoroughly mixed. Also, commercially available 0.005% calcipotriol (DOVONEX) and commercially available 0.005% calcipotriol was supplemented with 5% retinyl palmitate and employed in treating psoriasis. Two different and distant psoriatic spots were selected on the skin of patients diagnosed with psoriasis for different treatment. Each patient used two type of creams twice a day, one cream on each selected spot.

Group I consisting of five patients applied on one selected spot (spot A) control LUBRIDERM cream and on the other selected spot (spot B) cream containing 0.1% retinoic acid. None of the patients showed any improvement in either spots even after 12 weeks of treatment.

Group II consisting of five patients applied on one selected spot (spot A) control LUBRIDERM cream and on the other selected spot (spot B) cream containing 0.1% retinyl palmitate. No change in spot A was observed after 4 weeks of treatment. Three out of five patients showed mild improvement in itching after 3 days in spot B but no improvement in stopping scaling which results from cellular hyperproliferation.

Group III consisting of five patients applied on one selected spot (spot A) control LUBRIDERM cream and on the other selected spot (spot B) cream containing 1% retinyl palmitate. No change in spot A was observed after 4 weeks of treatment. Four out of five patients showed good improvement in itching after 3 days in spot B but no improvement in stopping scaling which results from cellular hyperproliferation.

Group IV consisting of five patients applied on one selected spot (spot A) control LUBRIDERM cream and on the other selected spot (spot B) cream containing 5% retinyl palmitate. No change in spot A was observed after 4 weeks of treatment. Five out of five patients showed good improvement in itching after 3 days in spot B but no improvement in stopping scaling which results from cellular hyperproliferation.

Group V consisting of five patients applied on one selected spot (spot A) control LUBRIDERM cream and on the other selected spot (spot B) cream containing 0.005% calcipotriol. No change in spot A was observed after 4 weeks of treatment. Two out of five patients showed partial clearance (average of 35% of spot area) in spot B after 4 weeks of treatment. However, even in the spots showing improvement and partial clearance, a certain amount of scaling is still occurring.

Group VI consisting of five patients applied on one selected spot (spot A) a cream containing 0.0025% calcipotriol and on the other selected spot (spot B) cream containing 0.0025% calcipotriol and 0.1% retinyl palmitate. One out of five patients showed partial clearance (about 20% of spot area) in spot A after 4 weeks of treatment. However, even in spot A that is showing improvement and partial clearance, a certain amount of scaling is still occurring. Two out of Five patients showed considerable amount of clearance (about 40% of spot area) in spot B and with little scaling and itching.

Group VII consisting of five patients applied on one selected spot (spot A) a cream containing 0.0025% calcipotriol and on the other selected spot (spot B) cream containing 0.0025% calcipotriol and 0.5% retinyl palmitate. Two out of five patients showed partial clearance (about 25% of spot area) in spot A after 4 weeks of treatment. However, even in spots A that are showing improvement and partial clearance, a certain amount of scaling is still occurring. Three out of Five patients showed considerable amount of clearance (about 50% of spot area) in spot B and with barely noticeable scaling and no itching.

Group VIII consisting of five patients applied on one selected spot (spot A) a cream containing 0.0025% calcipotriol and on the other selected spot (spot B) cream containing 0.0025% calcipotriol and 1% retinyl palmitate. Two out of five patients showed partial clearance (about 20% of spot area) in spot A after 4 weeks of treatment. However, even in spots A that are showing improvement and partial clearance, a certain amount of scaling is still occurring. Four out of Five patients showed considerable amount of clearance (about 50% of spot area) in spot B and with barely noticeable scaling and no itching.

Group IX consisting of five patients applied on one selected spot (spot A) a cream containing 0.0025% calcipotriol and on the other selected spot (spot B) cream containing 0.0025% calcipotriol and 5% retinyl palmitate. One out of five patients showed partial clearance (about 30% of spot area) in spot A after 4 weeks of treatment. However, even in spot A that is showing improvement and partial clearance, a certain amount of scaling is still occurring. Five out of Five patients showed considerable amount of clearance (average about 85% of spot area and one complete clearance) in spot B and with no scaling and itching.

Group X consisting of five patients applied on one selected spot (spot A) a cream containing 0.0025% calcipotriol and on the other selected spot (spot B) cream containing 0.0025% calcipotriol and 10% retinyl palmitate. One out of five patients showed partial clearance (about 15% of spot area) in spot A after 4 weeks of treatment. However, even in spot A that is showing improvement and partial clearance, a certain amount of scaling is still occurring. Five out of Five patients showed considerable amount of clearance (average about 90% of spot area and two complete clearance) in spot B and with no scaling and itching.

Group XI consisting of five patients applied on one selected spot (spot A) a cream containing 0.0025% calcipotriol and on the other selected spot (spot B) cream containing 0.0025% calcipotriol and 0.1% 4-oxo-retinol. One out of five patients showed partial clearance (about 20% of spot area) in spot A after 4 weeks of treatment. However, even in spot A that is showing improvement and partial clearance, a certain amount of scaling is still occurring. Five out of Five patients showed considerable amount of clearance (average about 95% of spot area and four complete clearances) in spot B and with no scaling and itching.

Group XII consisting of five patients applied on one selected spot (spot A) a cream containing 0.1% 4-oxo-retinol and on the other selected spot (spot B) cream containing 0.0025% calcipotriol and 0.1% 4-oxo-retinol. One out of five patients showed partial clearance (about 10% of spot area) in spot A after 4 weeks of treatment. However, even in spot A that is showing improvement and partial clearance, a significant amount of scaling is still occurring. Five out of Five patients showed complete clearances (100%) in spot B and with no scaling and itching.

Group XIII consisting of five patients applied on one selected spot (spot A) a cream containing 0.1% 4-oxo-retinol and on the other selected spot (spot B) cream containing 0.002% calcitriol and 0.1% 4-oxo-retinol. One out of five patients showed partial clearance (about 15% of spot area) in spot A after 4 weeks of treatment. However, even in spot A that is showing improvement and partial clearance, a significant amount of scaling is still occurring. Five out of Five patients showed complete clearances (100%) in spot B and with no scaling and itching.

Group XIV consisting of five patients applied on one selected spot (spot A) a cream containing 0.1% 4-hydroxy-retinol and on the other selected spot (spot B) cream containing 0.002% calcitriol and 0.1% 4-hydroxy-retinol. One out of five patients showed partial clearance (about 10% of spot area) in spot A after 4 weeks of treatment. However, even in spot A that is showing improvement and partial clearance, a significant amount of scaling is still occurring. Four out of Five patients showed complete clearances with an average clearance of 95% in spot B and with no scaling and itching.

Group XV consists of five patients applied on one selected spot (spot A) a cream containing 0.0025% calcipotriol and on the other selected spot (spot B) cream containing 0.0025% calcipotriol and 0.1% all-trans retinoic acid. Two out of five patients showed partial clearance (about 15% of spot area) in spot A after 4 weeks of treatment. However, even in spots A that are showing improvement and partial clearance, a certain amount of scaling is still occurring. Similar results were obtained in spot B after 4 weeks of treatment (about 20% partial clearance with persistence of scaling).

Group XVI consisting of five patients applied on one selected spot (spot A) a cream containing 0.005% calcipotriol and on the other selected spot (spot B) cream containing 5% Cholecalciferol and 5% retinyl palmitate. Two out of five patients showed partial clearance (about 15% of spot area) in spot A after 4 weeks of treatment. However, even in spots A that are showing improvement and partial clearance, a certain amount of scaling is still occurring. Five out of Five patients showed considerable amount of clearance (average about 75% of spot area and one complete clearance) in spot B and with no scaling and itching. The rest of the spots showed no improvement.

This data clearly indicates the synergistic effect of vitamin D analogs with retinyl esters above 0.1%, 4-oxo-retinol, or 4-hydroxy-retinol in treating psoriasis. However, there were no synergistic effects with of vitamin D analogs with retinoic acid. Similar experiments were carried out using retinol rather than retinyl palmitate with similar results.

EXAMPLE 3

Three patients diagnosed with eczema were treated with cream containing 0.0025% calcipotriol and 5% retinyl palmitate. A significant improvement was noticed in all three patients within 5 days and two had normal-looking skin after two weeks. A similar results was also observed with patients treated with 0.002% calcitriol and 0.1% 4-oxo-retinol. Treatment with 5% retinyl palmitate, with 0.1% 4-oxo-retinol without a vitamin D analog, or with a vitamin D analog and 0.1% all-trans retinoic acid did not result in any significant improvements over the same period of time.

EXAMPLE 4

A patient diagnosed with atopic dermatitis was treated with cream containing 0.05% calcipotriol and 0.1% 4-oxo-retinol. A significant improvement was noticed in within 1 week and the appearance of normal-looking skin after two weeks.

EXAMPLE 5

Various types of human melanoma, breast cancer and prostate cancer cells will be cultured according to standardized procedures. These cells will be incubated with in the presence of various concentrations of retinol, retinoic acid, retinyl esters, calcitriol or a combination thereof. Cell growth of at least some of these cells will be shown to be significantly inhibited in the presence of calcitriol and either 4-oxo-retinol or high concentrations of retinol (about $10^{-5}$ M) as compared with cells incubated in the absence of the above compounds or in the presence of each of the above compounds alone.

EXAMPLE 6

Patients with breast cancer, prostate cancer or leukemia, particularly acute promyelocytic leukemia treated with a combination of oral doses of 4-oxo-retinol or 4-hydroxy-retinol (100 mg/square meter) and oral doses of calcitriol will have a reduced tumor burden, undergo prolonged remission or are permanently cured.

EXAMPLE 7

Current systemic chemotherapy regimens are unable to prolong survival of patients with advanced head and neck cancer. Patients treated with a combination of oral doses of 4-oxo-retinol or 4-hydroxy-retinol (100 mg/square meter) and oral doses of calcitriol will survive beyond the median of 4–6 months, and/or have reduced tumor burden during the period during which this treatment is administered.

EXAMPLE 8

Patients with deep (cystic acne) treated with a combination of oral doses of 4-oxo-retinol or 4-hydroxy-retinol (100 mg/square meter) and oral doses of calcitriol will have greater than 50% mean reduction in lesion counts at the end of 3 to 6 months treatment period and in some cases complete treatment will occur after discontinuation of therapy. A very prolonged remission and permanent cure for some will be obtained.

EXAMPLE 9

Patients with psoriatic arthritis treated with a combination of oral doses of 4-oxo-retinol or 4-hydroxy-retinol (50–100 mg/square meter) and oral doses of calcitriol exhibit fewer tender joints and a decreased duration of morning stiffness.

EXAMPLE 10

Individuals suffering from male pattern baldness treated once or twice daily with a topical formulation of any of the compositions of the present invention, particularly with a topical formulation containing 0.002% calcitriol and 0.1% 4-oxo-retinol or 0.1% 4-hydroxy-retinol will regrow a cosmetically significant amount of hair within 6–9 months of treatment. Similar results would be expected with oral formulations.

EXAMPLE 11

Individuals with gray hair treated once or twice daily with a topical formulation of any of the compositions of the present invention, particularly with a topical formulation containing 0.002% calcitriol and 0.1% 4-oxo-retinal or 0.1% 4-hydroxy-retinol will grow hair having the natural color within 6–9 months of treatment. Similar results would be expected with oral formulations.

The invention has been described in terms of preferred embodiments thereof, but is more broadly applicable as will be understood by those skilled in the art. The scope of the invention is therefore limited only by the following claims.

What is claimed is:

1. A composition comprising a vitamin D analog and a retinoid, wherein:
   (a) the vitamin D analog is capable of binding a vitamin D receptor or being converted in vivo into a compound capable of binding a vitamin D receptor; and
   (b) the retinoid is selected from the group consisting of retinoid D with an alcohol $CH_2OH$ terminal side chain, an ester of retinoid D having an ester bond, an ether of retinoid D having an ether bond, and retinoid D where the alcohol $CH_2OH$ terminal side chain is replaced with an aldehyde CHO terminal side chain, wherein each of the ester bond and the ether bond is formed with the oxygen at the terminal side chain of Retinoid D and wherein said retinoid D with the alcohol $CH_2OH$ terminal side chain has the structure:

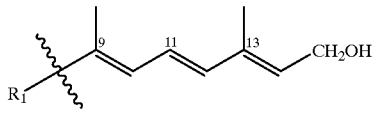

wherein the configuration at the 7-, 9-, 11- and 13-position double bonds is independently Z or E and wherein $R_1$ is selected from the group consisting of:

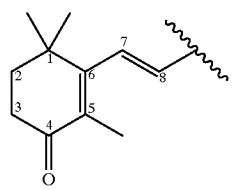

wherein the keto group at the 4-position is free or protected; and

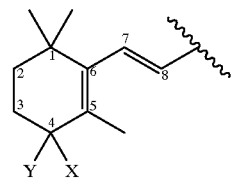

wherein X is selected from the group consisting of hydrogen and $C_{1-6}$-alkyl and Y is selected from the group consisting of hydroxy and $C_{1-6}$-alkyoxyl and wherein the absolute configuration at the 4-position is independently R or S.

2. The composition of claim 1, wherein the retinoid is retinoid D with an alcohol $CH_2OH$ terminal side chain.

3. The composition of claim 1, wherein the retinoid is selected from the group consisting of 4-oxo-retinol, 4-oxo-retinal, and 4-oxo-retinyl ester.

4. A topical composition according to claim 1.

5. The composition of claim 1, wherein the vitamin D analog is selected from the group consisting of cholecalciferol, calcifediol, calcitriol, calcipotriol, ergocalciferol, dihydrotachysterol, 1,25-dihydroxyergocalciferol, and 25-hydroxydihydrotachysterol.

6. The composition of claim 1, wherein the vitamin D analog is calcitriol.

7. The composition of claim 1, wherein the vitamin D analog is calcipotriol.

8. The composition of claim 1, wherein the retinoid is 4-oxo-retinol.

9. The composition of claim 1, wherein the vitamin D analog is calcitriol or calcipotriol and the retinoid is a 4-oxo-retinol.

10. The composition of claim 1, wherein the vitamin D analog is a vitamin D3 analog.

11. The composition of claim 1, wherein the retinoid is 4-oxo-retinal.

12. The composition of claim 1, wherein the retinoid is 4-methoxy-retinol.

13. A method of treating a subject suffering from a disorder characterized by abnormal cell-proliferation and/or cell-differentiation, comprising administering to the subject in need of such treatment a vitamin D analog and a retinoid, wherein the combination of the vitamin D analog and the retinoid is an effective combination and the retinoid and the vitamin D analog are administered simultaneously or at different times and wherein:
   (a) the vitamin D analog is capable of binding a vitamin D receptor or being converted in vivo into a compound capable of binding a vitamin D receptor; and
   (b) the retinoid is selected from the group consisting of retinoid D with an alcohol $CH_2OH$ terminal side chain, an ester of retinoid D having an ester bond, an ether of retinoid D having an ether bond, and retinoid D where the alcohol $CH_2OH$ terminal side chain is replaced with an aldehyde CHO terminal side chain, wherein each of the ester bond and the ether bond is formed with the oxygen at the terminal side chain of Retinoid D and wherein said retinoid D with the alcohol $CH_2OH$ terminal side chain has the structure:

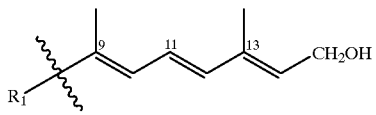

wherein the configuration at the 7-, 9-, 11- and 13-position double bonds is independently Z or E and wherein $R_1$ is selected from the group consisting of:

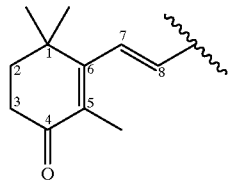

wherein the keto group at the 4-position is free or protected; and

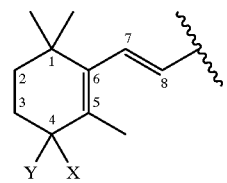

wherein X is selected from the group consisting of hydrogen and $C_{1-6}$-alkyl and Y is selected from the group consisting of hydroxy and $C_{1-6}$-alkyoxyl and wherein the absolute configuration at the 4-position is independently R or S.

14. The method of claim 13, wherein the retinoid is retinoid D with an alcohol $CH_2OH$ terminal side chain.

15. The method of claim 13, wherein the retinoid is selected from the group consisting of 4-oxo-retinol, 4-oxo-retinal, and 4-oxo-retinyl ester.

16. The method of claim 13, wherein the vitamin D analog is selected from the group consisting of cholecalciferol, calcifediol, calcitriol, calcipotriol, ergocalciferol, dihydrotachysterol, 1,25-dihydroxyergocalciferol, and 25-hydroxydihydrotachysterol.

17. The method of claim 13, wherein the vitamin D analog is calcitriol.

18. The method of claim 13, wherein the vitamin D analog is calcipotriol.

19. The method of claim 13, wherein the vitamin D analog is a vitamin D3 analog.

20. The method of claim 13, wherein the retinoid is 4-oxo-retinol.

21. The method of claim 13, wherein the retinoid is 4-hydroxy-retinol.

22. The method of claim 13, wherein the retinoid is 4-methoxy-retinol.

23. The method of claim 13, wherein the vitamin D analog is calcitriol or calcipotriol and the retinoid is a 4-oxo-retinol.

24. The method of claim 13, wherein the retinoid is administered topically.

25. A method of treating a subject suffering from a disorder selected from the group consisting of psoriasis, acne, atopic dermatitis, eczema, rosacea, actinic keratosis, seborrheic dermatitis, and congenital keratinization disorders, comprising administering to the subject in need of such treatment a vitamin D analog and a retinoid, wherein the combination of the vitamin D analog and the retinoid is an effective combination and the retinoid and the vitamin D analog are administered simultaneously or at different times and wherein:

(a) the vitamin D analog is capable of binding a vitamin D receptor or being converted in vivo into a compound capable of binding a vitamin D receptor; and (b) the retinoid is selected from the group consisting of retinoid D with an alcohol $CH_2OH$ terminal side chain, an ester of retinoid D having an ester bond, an ether of retinoid D having an ether bond, and retinoid D where the alcohol $CH_2OH$ terminal side chain is replaced with an aldehyde CHO terminal side chain, wherein each of the ester bond and the ether bond is formed with the oxygen at the terminal side chain of Retinoid D and wherein said retinoid D with the alcohol $CH_2OH$ terminal side chain has the structure:

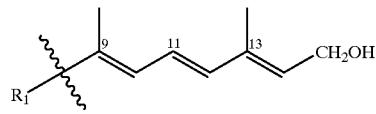

wherein the configuration at the 7-, 9-, 11- and 13-position double bonds is independently Z or E and wherein $R_1$ is selected from the group consisting of:

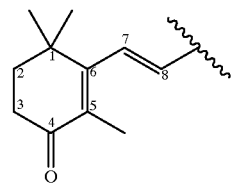

wherein the keto group at the 4-position is free or protected; and

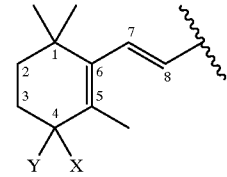

wherein X is selected from the group consisting of hydrogen and $C_{1-6}$-alkyl and Y is selected from the group consisting of hydroxy and $C_{1-6}$-alkyoxyl and wherein the absolute configuration at the 4-position is independently R or S.

26. The method of claim 25, wherein the retinoid is retinoid D with an alcohol $CH_2OH$ terminal side chain.

27. The method of claim 26, wherein the retinoid is 4-oxo-retinol.

28. The method of claim 26, wherein the retinoid is 4-hydroxy-retinol.

29. The method of claim 26, wherein the retinoid is 4-methoxy-retinol.

30. The method of claim 26, wherein the vitamin D analog is calcitriol or calcipotriol and the retinoid is a 4-oxo-retinol.

31. The method of claim 25, wherein the retinoid is selected from the group consisting of 4-oxo-retinol, 4-oxo-retinal, and 4-oxo-retinyl ester.

32. The method of claim 25, wherein the vitamin D analog is selected from the group consisting of cholecalciferol, calcifediol, calcitriol, calcipotriol, ergocalciferol, dihydrotachysterol, 1,25-dihydroxyergocalciferol, and 25-hydroxydihydrotachysterol.

33. The method of claim 25, wherein the vitamin D analog is calcitriol.

34. The method of claim 33, wherein the disorder is psoriasis.

35. The method of claim 33, wherein the disorder is eczema.

36. The method of claim 25, wherein the vitamin D analog is calcipotriol.

37. The method of claim 25, wherein the vitamin D analog is a vitamin D3 analog.

38. The method of claim 25, wherein the disorder is psoriasis.

39. The method of claim 25, wherein the retinoid is applied topically.

40. The method of claim 25, wherein the disorder is eczema.

41. The method of claim 25, wherein the disorder is acne.

42. The method of claim 25, wherein the disorder is atopic dermatitis.

43. A method of treating one or more conditions of the skin selected from the group consisting of dry skin, photodamaged skin, age spots, aged skin, inflexibility of stratum corneum, wrinkles, fine lines, actinic blemishes, skin dyschromias, and ichthyosis, comprising applying to the skin having said one or more condition a vitamin D analog and a retinoid, wherein the combination of the vitamin D analog and the retinoid is an effective combination and the retinoid and the vitamin D analog are administered simultaneously or at different times and, wherein:

(a) the vitamin D analog is capable of binding a vitamin D receptor or being converted in vivo into a compound capable of binding a vitamin D receptor; and (b) the retinoid is selected from the group consisting of retinoid D with an alcohol $CH_2OH$ terminal side chain, an ester of retinoid D having an ester bond, an ether of retinoid D having an ether bond, and retinoid D where the alcohol $CH_2OH$ terminal side chain is replaced with an aldehyde CHO terminal side chain, wherein each of the ester bond and the ether bond is formed with the oxygen at the terminal side chain of Retinoid D and wherein said retinoid D with the alcohol $CH_2OH$ terminal side chain has the structure:

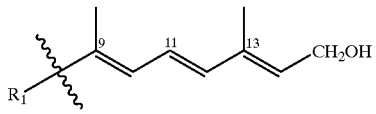

wherein the configuration at the 7-, 9-, 11- and 13-position double bonds is independently Z or E and wherein $R_1$ is selected from the group consisting of:

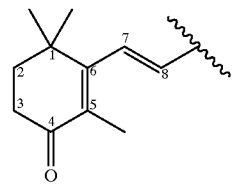

wherein the keto group at the 4-position is free or protected; and

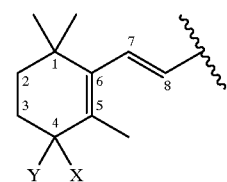

wherein X is selected from the group consisting of hydrogen and $C_{1-6}$-alkyl and Y is selected from the group consisting of hydroxy and $C_{1-6}$-alkyoxyl and wherein the absolute configuration at the 4-position is independently R or S.

44. The method of claim 43, where in the retinoid is retinoid D with an alcohol $CH_2OH$ terminal side chain.

45. The method of claim 43, wherein the retinoid is selected from the group consisting of 4-oxo-retinol, 4-oxo-retinal, and 4-oxo-retinyl ester.

46. The method of claim 44, wherein the vitamin D analog is selected from the group consisting of cholecalciferol, calcifediol, calcitriol, calcipotriol, ergocalciferol, dihydrotachysterol, 1,25-dihydroxyergocalciferol, and 25-hydroxydihydrotachysterol.

47. The method of claim 44, wherein the vitamin D analog is calcitriol.

48. The method of claim 44, wherein the vitamin D analog is calcipotriol.

49. The method of claim 44, wherein the retinoid is 4-oxo-retinol.

50. The method of claim 44, wherein the retinoid is 4-hydroxy-retinol.

51. The method of claim 44, wherein the retinoid is 4-methoxy-retinol.

52. The method of claim 44, wherein the vitamin D analog is calcitriol or calcipotriol and the retinoid is a 4-oxo-retinol.

53. The method of claim 44, wherein the vitamin D analog is a vitamin D3 analog.

* * * * *